(12) United States Patent
Michihata (10) Patent No.: US 11,737,646 B2
(45) Date of Patent: Aug. 29, 2023

(54) MEDICAL IMAGE PROCESSING DEVICE AND MEDICAL OBSERVATION SYSTEM

(71) Applicant: Sony Olympus Medical Solutions Inc., Tokyo (JP)

(72) Inventor: Taihei Michihata, Kanagawa (JP)

(73) Assignee: SONY OLYMPUS MEDICAL SOLUTIONS INC., Tokyo (JP)

(*) Notice: Subject to any disclaimer, the term of this patent is extended or adjusted under 35 U.S.C. 154(b) by 419 days.

(21) Appl. No.: 16/729,522

(22) Filed: Dec. 30, 2019

(65) Prior Publication Data
US 2020/0286226 A1 Sep. 10, 2020

(30) Foreign Application Priority Data
Mar. 7, 2019 (JP) ................................ 2019-042014

(51) Int. Cl.
| | |
|---|---|
| *A61B 1/00* | (2006.01) |
| *A61B 1/06* | (2006.01) |
| *G06T 7/00* | (2017.01) |
| *A61B 1/05* | (2006.01) |
| *A61B 1/04* | (2006.01) |

(52) U.S. Cl.
CPC ........ *A61B 1/000094* (2022.02); *A61B 1/043* (2013.01); *A61B 1/05* (2013.01); *A61B 1/0638* (2013.01); *G06T 7/0012* (2013.01); *G06T 2207/10064* (2013.01); *G06T 2207/10068* (2013.01)

(58) Field of Classification Search
CPC .......................................... G06T 2207/10064
See application file for complete search history.

(56) References Cited

U.S. PATENT DOCUMENTS

| | | | | |
|---|---|---|---|---|
| 4,885,634 A | * | 12/1989 | Yabe .................... | A61B 1/0005 348/270 |
| 6,364,829 B1 | * | 4/2002 | Fulghum .............. | A61B 1/0669 600/178 |
| 6,371,908 B1 | * | 4/2002 | Furusawa ............ | A61B 5/0059 348/E9.01 |

(Continued)

FOREIGN PATENT DOCUMENTS

| | | |
|---|---|---|
| JP | 2002291682 A | 10/2002 |
| JP | 2003079568 A | 3/2003 |

(Continued)

*Primary Examiner* — John P Leubecker
*Assistant Examiner* — Jae Woo
(74) *Attorney, Agent, or Firm* — Xsensus LLP (57) ABSTRACT

A medical image processing device includes a processor configured to: acquire a first captured image captured based on light from an observation target irradiated with light in a first wavelength band, the observation target emitting fluorescence upon being irradiated with excitation light in a second wavelength band; acquire a second captured image captured based on the excitation light and the fluorescence from the observation target irradiated with the excitation light; specify a target area in which a pixel level is not lower than a predetermined threshold, in the first captured image; and generate, for an area at a same position as the target area, a superimposed image only including pixels in the target area in the first captured image, among pixels in the area at the same position as the target area in the second captured image and pixels in the target area in the first captured image.

11 Claims, 6 Drawing Sheets

(56) References Cited

U.S. PATENT DOCUMENTS

| | | | | |
|---|---|---|---|---|
| 6,465,968 | B1* | 10/2002 | Sendai | A61B 5/0071 600/160 |
| 6,821,245 | B2* | 11/2004 | Cline | A61B 1/06 600/181 |
| 7,086,954 | B2* | 8/2006 | Gobush | G01P 3/38 473/198 |
| 8,107,158 | B2* | 1/2012 | Yamazaki | A61B 1/000094 356/73 |
| 8,131,349 | B2* | 3/2012 | Okawa | A61B 1/0638 600/478 |
| 8,300,309 | B2* | 10/2012 | Haisch | G02B 21/18 356/498 |
| 8,834,359 | B2* | 9/2014 | Ozawa | A61B 1/0653 382/128 |
| 8,936,548 | B2* | 1/2015 | Ozawa | A61B 1/0638 600/478 |
| 8,994,801 | B2* | 3/2015 | Tanaka | A61B 1/000094 600/109 |
| 9,313,388 | B2* | 4/2016 | Shida | A61B 1/00009 |
| 9,513,219 | B2* | 12/2016 | Ishihara | A61B 1/0005 |
| 9,516,235 | B2* | 12/2016 | Shida | G01N 21/6456 |
| 9,588,046 | B2* | 3/2017 | Ishihara | A61B 1/00009 |
| 10,849,712 | B2* | 12/2020 | Sugie | A61B 1/0005 |
| 2005/0059894 | A1* | 3/2005 | Zeng | A61B 5/0075 600/476 |
| 2007/0276259 | A1* | 11/2007 | Okawa | A61B 1/043 600/476 |
| 2012/0136209 | A1* | 5/2012 | Kostenich | G01J 3/0208 600/109 |
| 2012/0296218 | A1* | 11/2012 | Ishihara | G01N 21/6456 600/478 |
| 2012/0330165 | A1* | 12/2012 | Watanabe | A61B 1/043 600/476 |
| 2013/0002844 | A1* | 1/2013 | Shida | A61B 1/0005 348/E7.085 |
| 2013/0026390 | A1* | 1/2013 | Ono | A61B 1/000095 250/200 |
| 2013/0096376 | A1* | 4/2013 | Takei | A61B 1/043 600/103 |
| 2013/0116508 | A1* | 5/2013 | Shida | A61B 1/00045 600/109 |
| 2013/0235258 | A1* | 9/2013 | Shida | A61B 1/043 348/370 |
| 2014/0028824 | A1* | 1/2014 | Kubo | A61B 1/043 348/77 |
| 2014/0037179 | A1* | 2/2014 | Shida | A61B 1/00055 382/132 |
| 2014/0049626 | A1* | 2/2014 | Ishihara | G01N 21/64 348/68 |
| 2014/0078279 | A1* | 3/2014 | Shida | G06T 7/174 348/68 |
| 2014/0092226 | A1* | 4/2014 | Kuriyama | H04N 5/217 348/229.1 |
| 2014/0135609 | A1* | 5/2014 | Kostenich | A61B 5/0084 600/407 |
| 2014/0184769 | A1* | 7/2014 | Ishihara | G01N 21/64 348/68 |
| 2014/0213871 | A1* | 7/2014 | Watanabe | A61B 5/02042 600/371 |
| 2014/0301617 | A1* | 10/2014 | Shida | A61B 1/00009 382/128 |
| 2015/0042774 | A1* | 2/2015 | Sugano | G06T 5/50 348/68 |
| 2016/0007856 | A1* | 1/2016 | Ishihara | G02B 23/2469 600/476 |
| 2019/0376892 | A1* | 12/2019 | Ishikawa | G06T 7/0016 |
| 2020/0026062 | A1* | 1/2020 | Schuster | A61B 1/042 |
| 2020/0178781 | A1* | 6/2020 | Tabata | A61B 1/00009 |

FOREIGN PATENT DOCUMENTS

| | | |
|---|---|---|
| JP | 2012245161 A | 12/2012 |
| JP | 2015-029841 A | 2/2015 |
| WO | WO-2013035738 A1 | 3/2013 |
| WO | WO-2013100030 A1 | 7/2013 |
| WO | WO-2018230066 A1 | 12/2018 |

* cited by examiner

MEDICAL IMAGE PROCESSING DEVICE AND MEDICAL OBSERVATION SYSTEM

This application claims priority from Japanese Application No. 2019-042014, filed on Mar. 7, 2019, the contents of which are incorporated by reference herein in its entirety.

BACKGROUND

The present disclosure relates to a medical image processing device and a medical observation system.

A medical observation system for fluorescence observation has been known (see, for example, JP 2015-29841 A). Specifically, fluorescent substances, such as indocyanine green, are administered into a living body. Then, an observation target is irradiated with excitation light that excites the fluorescent substances, and a lesioned part where the fluorescent substances are accumulated is observed (see, for example, JP 2015-29841 A).

In the medical observation system (rigid endoscope system) described in JP 2015-29841 A, first and second captured images described below are each acquired, and a superimposed image is generated with corresponding pixels in the first and the second captured images superimposed on each other.

The first captured image is an image captured with an image sensor based on normal light, which is white light, reflected from an observation target irradiated with the normal light.

The second captured image is an image captured with a highly sensitive image sensor based on fluorescence from an observation target as a result of irradiation and excitation of the observation target with excitation light, for exciting the fluorescent substances such as indocyanine green. An optical filter (special light cut filter) for cutting (removing) the excitation light reflected from the observation target is provided on the upstream side of the highly sensitive image sensor on the optical path.

SUMMARY

The wavelength band (hereinafter, referred to as a cut band) of the optical filter for cutting light might deviate from the desired (designed) cut band, due to production tolerance, temperature change, aging, and the like. Thus, the cut band having deviated from the desired cut band might result in an image captured with the highly sensitive image sensor based not only on the fluorescence but also on a part of the excitation light that has passed through the optical filter.

In such a case, a portion of the observation target, other than the lesioned part, reflecting a large amount of excitation light to the highly sensitive image sensor (hereinafter, referred to as a highly reflective portion) is included in the second captured image, captured with the highly sensitive image sensor, together with the fluorescence. Thus, such a portion is recognized as the lesioned part. Thus, a superimposed image in which the first captured image and the above-described second captured image are superimposed on each other is an image involving a risk that the portion (the highly reflective portion described above) other than the lesioned part might be recognized as the lesioned part, and thus is unsuitable for observation.

Thus, a technique capable of generating a superimposed image suitable for observation has been called for.

Three is a need for a medical image processing device and a medical observation system that are capable of generating a superimposed image suitable for observation.

According to one aspect of the present disclosure, there is provided a medical image processing device including a processor including hardware, the processor being configured to: acquire a first image captured based on light from an observation target irradiated with light in a first wavelength band, the observation target emitting fluorescence upon being irradiated with excitation light in a second wavelength band different from the first wavelength band; acquire a second image captured based on the excitation light and the fluorescence from the observation target irradiated with the excitation light; specify a target area in which a pixel level is equal to or higher than a predetermined threshold, in the first image; generate a superimposed image by superimposing corresponding pixels in the first image and the second image on each other; and generate, for an area at a same position as the target area, the superimposed image only including pixels in the target area in the first image, among pixels in the area at the same position as the target area in the second image and pixels in the target area in the first image.

DETAILED DESCRIPTION

Hereinafter, modes for carrying out the present disclosure (hereinafter referred to as embodiments) will be described with reference to the drawings. The present disclosure is not limited to the embodiments described below. Furthermore, in the drawings, the same components are denoted with the same reference numerals.

First Embodiment

Schematic Configuration of Medical Observation System

Figure 1:
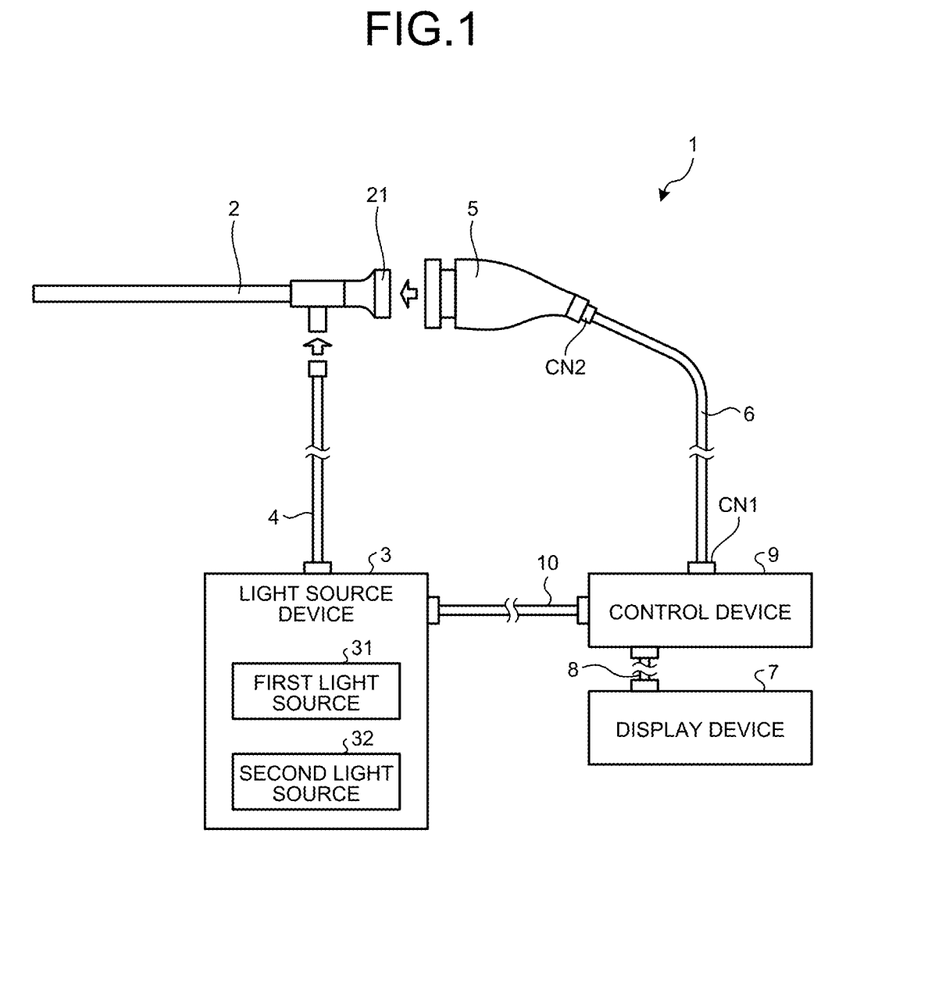
FIG. 1 is a diagram illustrating a configuration of a medical observation system according to a first embodiment.

FIG. 1 is a diagram illustrating a configuration of a medical observation system 1 according to this first embodiment The medical observation system 1 is a system that is used in the medical field for capturing (observing) an in-vivo image of a living body (observation target) that is a subject. As illustrated in FIG. 1, the medical observation system 1 includes an insertion portion 2, a light source device 3, a light guide 4, a camera head 5, a first transmission cable 6, a display device 7, a second transmission cable 8, a control device 9, and a third transmission cable 10.

In the first embodiment, the insertion portion 2 is formed by a rigid endoscope. Specifically, the insertion portion 2, to be inserted into a living body, has an elongated shape and is entirely rigid or is partially flexible and partially rigid. The insertion portion 2 is provided with an optical system that includes one or a plurality of lenses and focuses light from the subject.

The light source device 3 is connected to one end of the light guide 4 and supplies light to be emitted to the living body to one end of the light guide 4 under the control of the control device 9. As illustrated in FIG. 1, the light source device 3 includes a first light source 31 and a second light source 32.

The first light source 31 emits (outputs) normal light in a first wavelength band. In the first embodiment, the first light source 31 includes a light emitting diode (LED) that emits white light.

The second light source 32 emits (outputs) excitation light in a second wavelength band different from the first wavelength band. In the first embodiment, the second light source 32 includes a semiconductor laser that emits near-infrared excitation light in the near-infrared wavelength band. The near-infrared excitation light is excitation light that excites fluorescent substances such as indocyanine green. In addition, the fluorescent substances, such as indocyanine green, excited by the near-infrared excitation light emit fluorescence having a center wavelength longer than the center wavelength of the wavelength band of the near-infrared excitation light. Note that the wavelength band of the near-infrared excitation light and the wavelength band of the fluorescence may partially overlap or may not overlap at all.

In the light source device 3 according to the first embodiment, the first light source 31 is driven in a first period among the first and the second periods that are alternately repeated, under the control of the control device 9. Thus, in the first period, the light source device 3 emits normal light (white light). In the light source device 3, the second light source 32 is driven in the second period under the control of the control device 9. Thus, in the second period, the light source device 3 emits near-infrared excitation light.

In the first embodiment, the light source device 3 is formed to be separated from the control device 9. However, this should not be construed in a limiting sense, and a configuration where the light source device 3 is provided inside the control device 9 may be employed.

The light guide 4 has one end detachably connected to the light source device 3 and the other end detachably connected to the insertion portion 2. The light (normal light or near-infrared excitation light) supplied from the light source device 3 travels from one end to the other end of the light guide 4 to be supplied to the insertion portion 2. When the normal light (white light) is emitted in the living body, the normal light passing through the living body (normal light reflected in the living body) is focused by the optical system in the insertion portion 2. Hereinafter, for the sake of description, the normal light focused by the optical system in the insertion portion 2 is referred to as a first subject image. Furthermore, when near-infrared excitation light is emitted in the living body, the optical system in the insertion portion 2 focuses the near-infrared excitation light passing through the living body (near-infrared excitation light reflected in the living body) and the fluorescence emitted from the fluorescent substances, such as indocyanine green, as a result of exciting the fluorescent substances accumulated at the lesioned part in the living body. Hereinafter, for the sake of description, the near-infrared excitation light and the fluorescence focused by the optical system in the insertion portion 2 are referred to as a second subject image.

The camera head 5 corresponds to an imaging device according to the present disclosure. The camera head 5 is detachably connected to the proximal end (an eyepiece 21 (FIG. 1)) of the insertion portion 2. Under control of the control device 9, the camera head 5 captures the first subject image (normal light) and the second subject image (near-infrared excitation light and fluorescence) based on the light focused by the insertion portion 2, and outputs an image signal (RAW signal) as a result of the imaging. The image signal is, for example, an image signal of 4K or of a higher quality.

The detailed configuration of the camera head 5 will be described later.

The first transmission cable 6 has one end detachably connected to the control device 9 via a connector CN1 (FIG. 1) and the other end detachably connected to the camera head 5 via a connector CN2 (FIG. 1). The first transmission cable 6 transmits an image signal or the like output from the camera head 5 to the control device 9, and transmits a control signal, a synchronization signal, a clock, power, and the like, output from the control device 9, to the camera head 5.

Note that the transmission of the image signal or the like from the camera head 5 to the control device 9 through the first transmission cable 6 may be implemented by transmitting the image signal or the like as an optical signal or as an electrical signal. The same applies to transmission of the control signal, the synchronization signals, and the clock from the control device 9 to the camera head 5 through the first transmission cable 6.

The display device 7 is formed by a display using liquid crystals, organic electro luminescence (EL), or the like, and displays an image based on a video signal from the control device 9 under the control of the control device 9.

The second transmission cable 8 has one end detachably connected to the display device 7 and the other end detachably connected to the control device 9. The second transmission cable 8 transmits the video signal processed by the control device 9 to the display device 7.

The control device 9 corresponds to a medical image processing device according to the present disclosure. The control device 9 includes a central processing unit (CPU), a field-programmable gate array (FPGA), and the like, and comprehensively controls the operations of the light source device 3, the camera head 5, and the display device 7.

The detailed configuration of the control device 9 will be described later.

The third transmission cable 10 has one end detachably connected to the light source device 3 and the other end detachably connected to the control device 9. The third transmission cable 10 transmits the control signal from the control device 9 to the light source device 3.

Configuration of Camera Head

Next, the configuration of the camera head 5 will be described.

Figure 2:
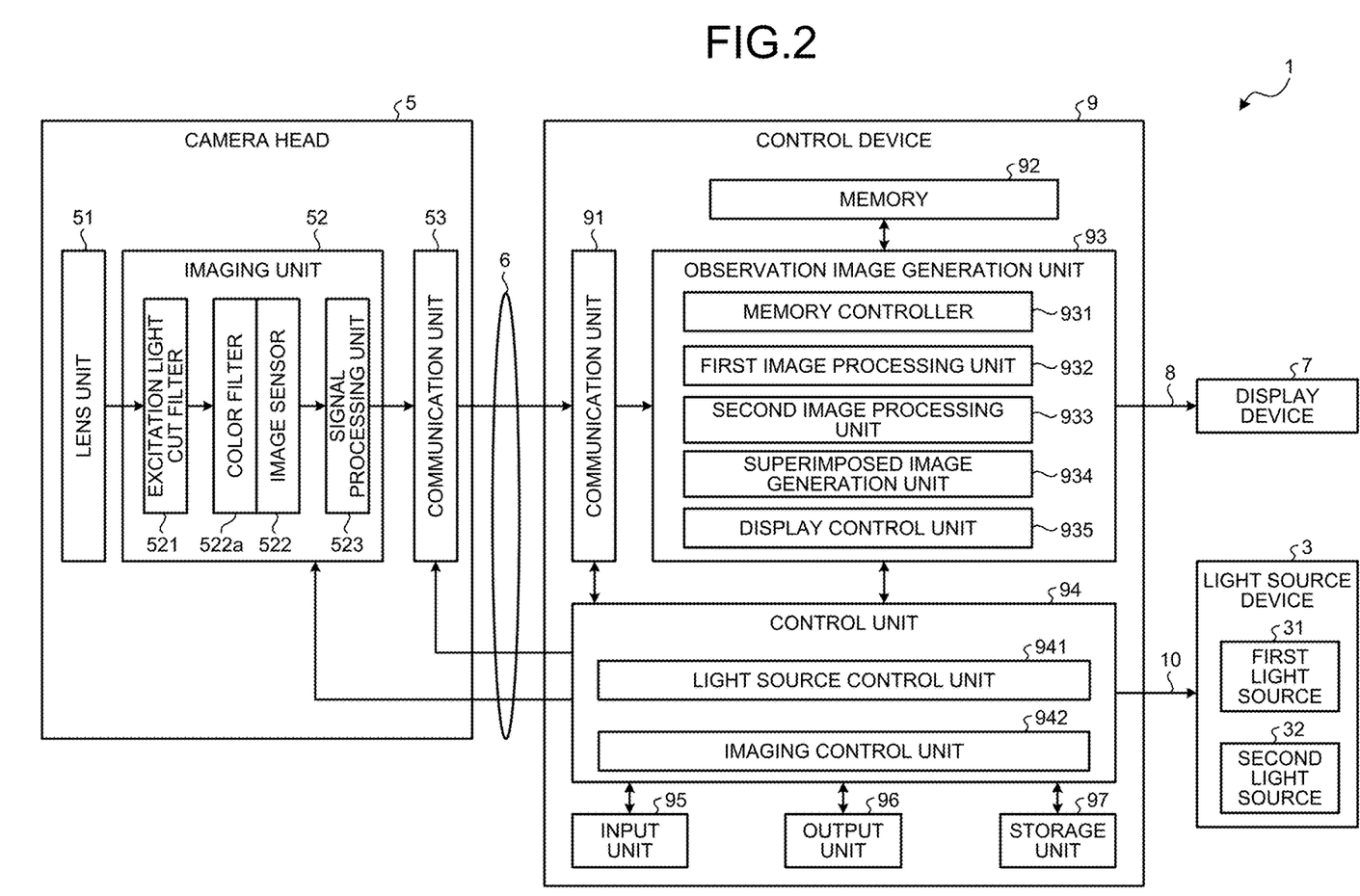
FIG. 2 is a block diagram illustrating configurations of a camera head and a control device.

FIG. 2 is a block diagram illustrating configurations of the camera head 5 and the control device 9.

In FIG. 2, for the sake of description, the connectors CN1 and CN2 between the control device 9 and the camera head 5 and the first transmission cable 6, as well as connectors between the control device 9 and the display device 7 and the second transmission cable 8 and connectors between the control device 9 and the light source device 3 and the third transmission cable 10 are omitted.

The camera head 5 includes a lens unit 51, an imaging unit 52, and a communication unit 53 as illustrated in FIG. 2.

The lens unit 51 includes one or a plurality of lenses, and forms the first subject image (normal light) and the second subject image (near-infrared excitation light and fluorescence), focused by the insertion portion 2, on an imaging surface of the imaging unit 52 (image sensor 522).

The imaging unit 52 captures an in-vivo image of the living body under the control of the control device 9. As illustrated in FIG. 2, the imaging unit 52 includes an excitation light cut filter 521, the image sensor 522, and a signal processing unit 523.

The excitation light cut filter 521 corresponds to a cut filter according to the present disclosure. The excitation light cut filter 521 is provided between the lens unit 51 and the image sensor 522, and includes a band stop filter that removes a predetermined wavelength band. Specifically, the excitation light cut filter 521 is disposed on the optical path of the near-infrared excitation light passing through the living body from the inside of the living body to the image sensor 522. Hereinafter, for the sake of description, a wavelength band that is cut (removed) by the excitation light cut filter 521 is referred to as a cut band. A wavelength band that is shorter than the cut band and passes through the excitation light cut filter 521 is referred to as a shorter side transmission band. A wavelength band that is longer than the cut band and passes through the excitation light cut filter 521 is referred to as a longer side transmission band.

This cut band includes at least a part of the wavelength band of the near-infrared excitation light. In the first embodiment, the cut band includes a part of the wavelength band of the near-infrared excitation light. The longer side transmission band includes a part of the wavelength band of near-infrared excitation light and the wavelength band of fluorescence. Furthermore, the shorter side transmission band includes the wavelength band of normal light (white light).

Thus, the excitation light cut filter 521 enables the first subject image (normal light (white light)) from the lens unit 51 to pass therethrough toward the image sensor 522. On the other hand, the excitation light cut filter 521 enables a part of the near-infrared excitation light and fluorescence for the second subject image (near-infrared excitation light and fluorescence) from the lens unit 51 to pass therethrough toward the image sensor 522.

The image sensor 522 includes a charge coupled device (CCD), a complementary metal oxide semiconductor (CMOS), or the like that receives light that has passed through the excitation light cut filter 521 and converts it into an electrical signal (analog signal).

This imaging surface (light reception surface) of the image sensor 522 is provided with a color filter 522a (FIG. 2). The color filter 522a includes three filter groups arranged in a predetermined format (Bayer array for example). The three filter groups are classified based on the wavelength bands of light (red (R), green (G), and blue (B)) passed therethrough.

Specifically, the color filter 522a includes an R filter group that mainly enables light in the R wavelength band to pass therethrough, a B filter group that mainly enables light in the B wavelength band to pass therethrough, a first G filter group (in the same row as the R filter group) that mainly enables light in the G wavelength band to pass therethrough, and a second G filter group (in the same row as the B filter group) that mainly enables light in the G wavelength band to pass therethrough. Hereinafter, for the sake of description, the first and the second G filter groups are collectively referred to as a G filter group.

The R, G, and B filter groups also enable near-infrared excitation light and fluorescence to pass therethrough. The image sensor 522 is not only sensitive to light in the R, G, and B wavelength bands, but is also sensitive to light in the wavelength bands of near-infrared excitation light and fluorescence.

The image sensor 522 performs imaging in each of the first and the second periods that are alternately repeated, in synchronization with the light emission timing of the light source device 3, under the control of the control device 9. Hereinafter, for the sake of description, an image generated by capturing the first subject image (normal light) in the first period with the image sensor 522 is referred to as a normal light image (corresponding to the first captured image according to the present disclosure). An image generated by capturing the second subject image (near-infrared excitation light and fluorescence) in the second period with the image sensor 522 is referred to as a fluorescent image (corresponding to the second captured image according to the present disclosure). In addition, the normal light image and the fluorescent image are collectively referred to as a captured image.

The signal processing unit 523 executes signal processing on the captured image (analog signal) generated by the image sensor 522 and outputs the captured image (RAW signal (digital signal)).

The communication unit 53 functions as a transmitter that transmits the captured image (RAW signal (digital signal)), output from the imaging unit 52, to the control device 9 through the first transmission cable 6. For example, the communication unit 53 includes a high-speed serial interface that performs captured image communication with the control device 9 through the first transmission cable 6 at a transmission rate of 1 Gbps or more.

Configuration of Control Device

Next, the configuration of the control device 9 will be described with reference to FIG. 2.

The control device 9 includes a communication unit 91, a memory 92, an observation image generation unit 93, a control unit 94, an input unit 95, an output unit 96, and a storage unit 97, as illustrated in FIG. 2.

The communication unit 91 functions as a receiver that receives the captured image (RAW signal (digital signal)) output from the camera head 5 (communication unit 53) through the first transmission cable 6. For example, the communication unit 91 includes a high-speed serial interface that performs captured image communication with the communication unit 53 at a transmission rate of 1 Gbps or more. Thus, the communication unit 91 corresponds to a first captured image acquisition unit and a second captured image acquisition unit according to the present disclosure.

The memory 92 includes, for example, a dynamic random access memory (DRAM) and the like. The memory 92 may temporarily store captured images output sequentially from the camera head 5 (communication unit 53) for a plurality of frames.

The observation image generation unit 93 processes the captured images (RAW signals (digital signals)) sequentially output from the camera head 5 (communication unit 53) and received by the communication unit 91, under the control of the control unit 94. As illustrated in FIG. 2, the observation image generation unit 93 includes a memory controller 931, a first image processing unit 932, a second image processing unit 933, a superimposed image generation unit 934, and a display control unit 935.

The memory controller 931 controls writing and reading of the captured image to and from the memory 92. More specifically, the memory controller 931 sequentially writes captured images (normal light image and fluorescent image) sequentially output from the camera head 5 (communication unit 53) and received by the communication unit 91, to the memory 92. In addition, the memory controller 931 reads the normal light image from the memory 92 at a predetermined timing, and inputs the read normal light image to the first image processing unit 932. Furthermore, the memory controller 931 reads the fluorescent image from the memory 92 at a predetermined timing, and inputs the read fluorescent image to the second image processing unit 933.

The first image processing unit 932 executes first image processing on the received normal light image (RAW signal (digital signal)).

Examples of the first image processing include optical black subtraction processing, white balance adjustment processing, demosaicing processing, color correction processing, gamma correction processing, and YC processing of converting an RGB signal (normal light image) into a luminance signal and a color difference signal (Y, $C_B/C_R$ signal). Furthermore, the first image processing includes area specifying processing described below.

The area specifying processing is processing of specifying a target area with a pixel level that is equal to or higher than a predetermined threshold (upper limit value in the first embodiment) in the normal light image. In other words, the upper limit value serves as a lower threshold for the specifying process to identify the target area.

An example of this pixel level includes information (pixel value) of any of R, G, and B components respectively corresponding to the R, G, and B filter groups of the color filter 522a, when the area specifying processing is executed on the normal light image before the demosaicing processing. Another example of the pixel level includes a luminance value corresponding to the RGB value (pixel value) or a Y signal (luminance signal), when the area specifying processing is executed on the normal light image after the demosaicing processing. That is, the area specifying processing may be executed before the demosaicing processing or may be executed after the demosaicing processing.

Thus, the first image processing unit 932 corresponds to an area specifying unit according to the present disclosure.

The second image processing unit 933 executes second image processing, different from the first image processing, on the received fluorescent image (RAW signal (digital signal)).

An example of the second image processing includes processing of generating a luminance signal (Y signal) only from the received fluorescent image (RAW signal (digital signal)), and enhancement processing of distinguishing a pixel position with a luminance value at or higher than a predetermined threshold in the entire image area (a pixel position where the fluorescent substances such as indocyanine green are excited) from other pixel positions. Furthermore, the second image processing includes area deleting processing described below.

The area deleting processing is processing of setting the luminance value of each pixel in an area corresponding to the target area in the normal light image specified by the area specifying processing to "0", in the fluorescent image.

The superimposed image generation unit 934 generates a superimposed image in which corresponding pixels in the normal light image after being subjected to the first image processing by the first image processing unit 932 and the fluorescent image after being subjected to the second image processing by the second image processing unit 933 are superimposed on each other over the entire area.

The display control unit 935 generates a video signal to be displayed based on the superimposed image generated by the superimposed image generation unit 934 under the control of the control unit 94. Then, the display control unit 935 outputs the video signal to the display device 7 via the second transmission cable 8.

The control unit 94 is formed by using, for example, a CPU, an FPGA, and the like, and outputs a control signal through the first to the third transmission cables 6, 8, and 10, to control operations of the light source device 3, the camera head 5, and the display device 7, and to control overall operations of the control device 9. As illustrated in FIG. 2, the control unit 94 includes a light source control unit 941 and an imaging control unit 942. The functions of the light source control unit 941 and the imaging control unit 942 will be described in "Operation of control device" described later.

The input unit 95 includes operation devices such as a mouse, a keyboard, and a touch panel, and receives a user operation by a user such as a doctor. Then, the input unit 95 outputs an operation signal corresponding to the user operation to the control unit 94.

The output unit 96 includes a speaker, a printer, or the like, and outputs various types of information.

The storage unit 97 stores a program executed by the control unit 94, information for the control unit 94 to execute processing, and the like.

Operation of Control Device

Next, the operation of the control device 9 described above will be described.

Figure 3:
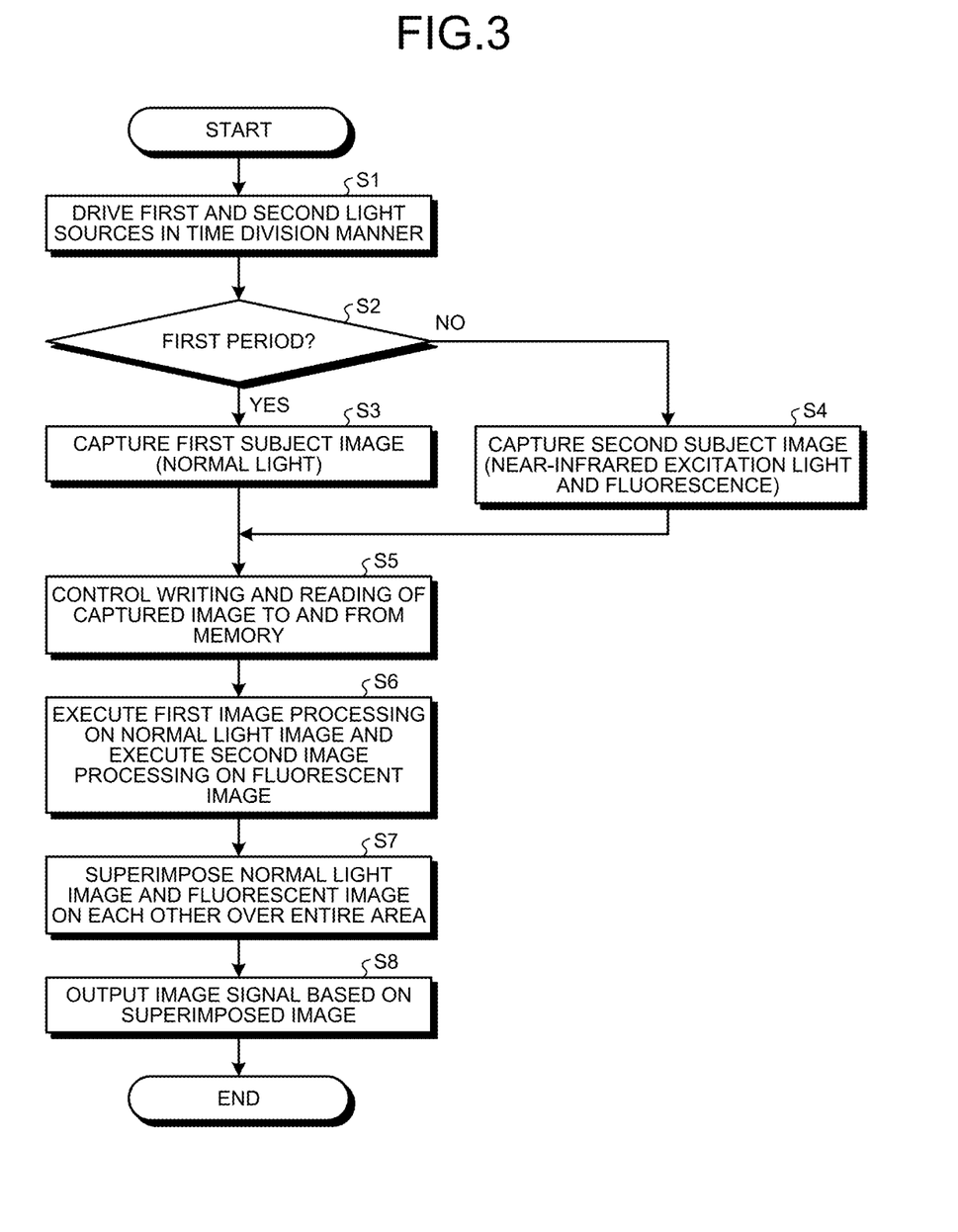
FIG. 3 is a flowchart illustrating an operation of the control device.
Figure 4:
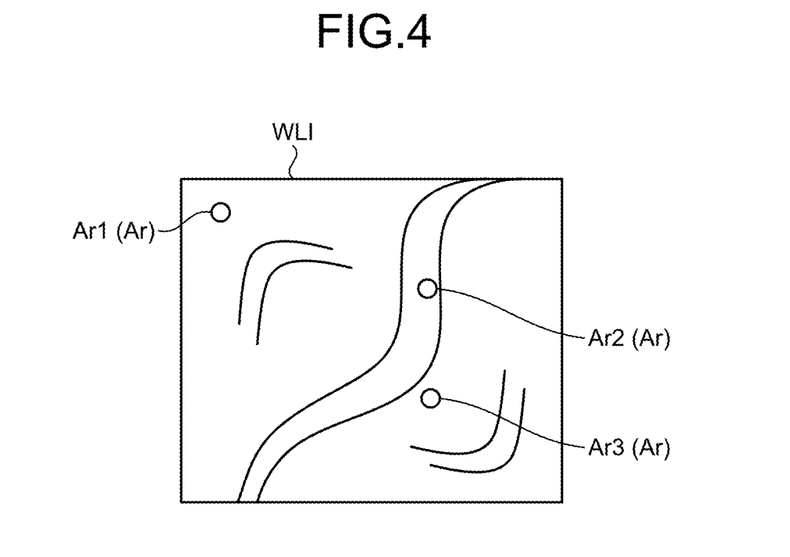
FIG. 4 is a diagram illustrating an operation of the control device.
Figure 5:
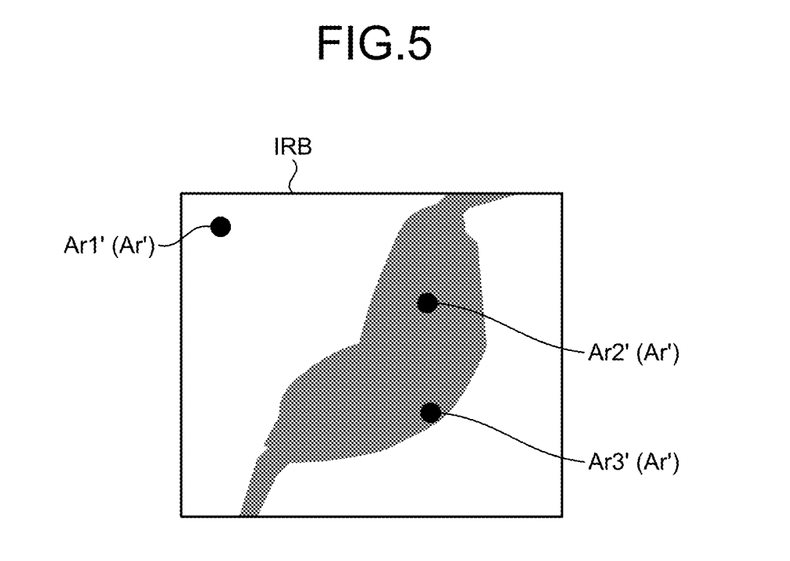
FIG. 5 is a diagram illustrating an operation of the control device.
Figure 6:
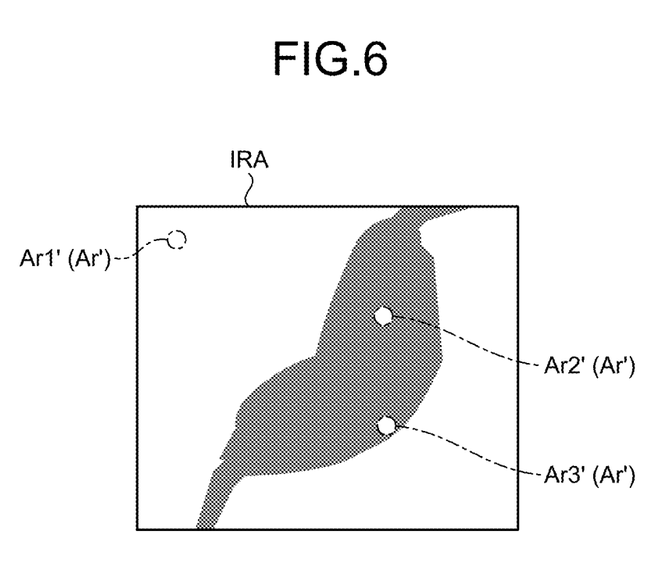
FIG. 6 is a diagram illustrating an operation of the control device.
Figure 7:
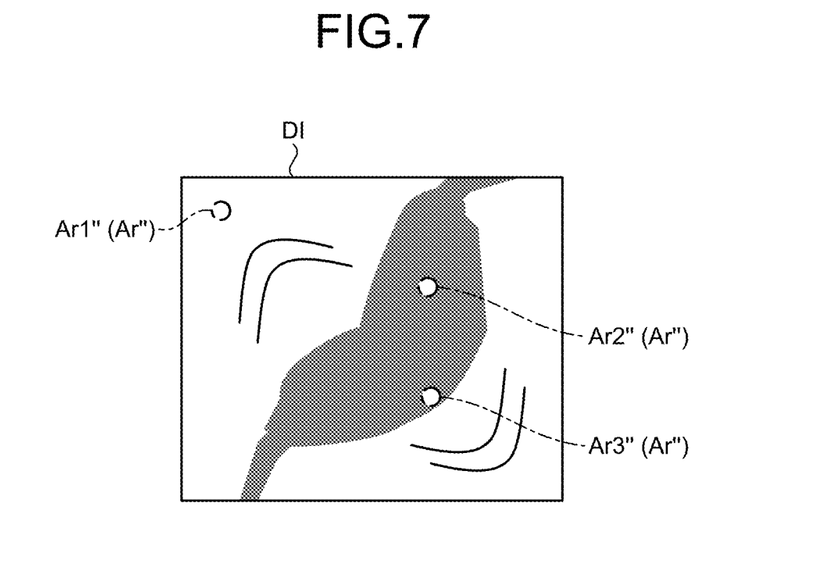
FIG. 7 is a diagram illustrating an operation of the control device.

FIG. 3 is a flowchart illustrating an operation of the control device 9. FIG. 4 to FIG. 6 are diagrams illustrating the operation of the control device 9. Specifically, FIG. 4 is a diagram illustrating a normal light image WLI one frame after the execution of the area specifying processing. FIG. 5 is a diagram illustrating a fluorescent image IRB one frame before the execution of the area deleting processing. FIG. 6 is a diagram illustrating a fluorescent image IRA one frame after the execution of the area deleting processing. The fluorescent images IRB and IRA illustrated in FIGS. 5 and 6 are expressed in gray scale with a tone closer to black representing a higher intensity (higher luminance value) of a component of at least one of the near-infrared excitation light and the fluorescence of the captured image. FIG. 7 is a diagram illustrating a superimposed image DI of a single frame generated by the superimposed image generation unit 934.

First of all, the light source control unit 941 drives the first and the second light sources 31 and 32 in a time division manner (Step S1). Specifically, in Step S1, based on the synchronization signal, the light source control unit 941 causes the first light source 31 to emit light in the first period of the first and the second periods that are alternately repeated, and causes the second light source 32 to emit light in the second period.

After Step S1, based on the synchronization signal, the imaging control unit 942 causes the image sensor 522 to capture the first and the second subject images respectively in the first and the second periods, in synchronization with the light emission timings of the first and the second light sources 31 and 32 based on the synchronization signal (Steps S2 to S4). Specifically, the image sensor 522 generates the normal light image by capturing the first subject image (normal light) in the first period (Step S2: Yes), that is, when the normal light (white light) is emitted in the living body (Step S3). On the other hand, the image sensor 522 generates the fluorescent image by capturing the second subject image (near-infrared excitation light and fluorescence) in the second period (Step S2: No), that is, when the near-infrared excitation light is emitted in the living body (Step S4).

After Steps S3 and S4, the memory controller 931 controls writing and reading of the captured image to and from the memory 92 based on the synchronization signal (Step S5).

After Step S5, the first and the second image processing units 932 and 933 execute the following processing (Step S6).

Specifically, the first image processing unit 932 executes the first image processing sequentially on the normal light images sequentially read from the memory 92 by the memory controller 931.

This first image processing includes the area specifying processing. Therefore, for example, as illustrated in FIG. 4, when the area specifying processing is executed on the normal light image WLI, target areas Ar in which the pixel level is at the upper limit value (in the example of FIG. 4, three target areas Ar1 to Ar3) are specified.

Note that the target area Ar is an area corresponding to a portion (hereinafter referred to as a highly reflective portion) in the observation target that reflects a large amount of normal light toward the insertion portion 2.

Furthermore, the second image processing unit 933 executes the second image processing sequentially on the fluorescent images (the fluorescent images IRB illustrated in FIG. 5 for example) sequentially read from the memory 92 by the memory controller 931.

Here, as described above, the excitation light cut filter 521 enables a part of the near-infrared excitation light from the lens unit 51 to pass therethrough toward the image sensor 522. A large amount of the near-infrared excitation light is reflected at the highly reflective portion of the observation target toward the insertion portion 2, as in the case of the normal light. Therefore, for example, in the fluorescent image IRB as illustrated in FIG. 5, the intensity of near-infrared excitation light is high (the luminance value is high) in an area Ar' (in the example of FIG. 5, three areas Ar1', Ar2', and Ar3', corresponding to the highly reflective portion in the observation target) at the same position as the target area Ar.

The second image processing includes the area deleting processing. Thus, for example, as illustrated in FIG. 6, when the area deleting processing is executed on the fluorescent image IRB, the fluorescent image IRA in which the luminance value of the area Ar' is set to "0" is generated. In FIG. 6, the area Ar' is illustrated by a one-dot chain line in order to express that the luminance value is set to "0".

After Step S6, the superimposed image generation unit 934 sequentially generates superimposed images (the superimposed images DI illustrated in FIG. 7 for example) by superimposing corresponding pixels in the normal light images (the normal light images WLI illustrated in FIG. 4 for example) sequentially output from the first image processing unit 932 and a corresponding one of the fluorescent images (the fluorescent image IRA illustrated in FIG. 6 for example) sequentially output from the second image processing unit 933 on each other over the entire area (step S7).

Specifically, as illustrated in FIG. 7, for an area Ar" (in the example in FIG. 7, areas Ar1", Ar2", and Ar3") at the same position as the target area Ar, the superimposed image generation unit 934 generates a superimposed image DI only including the pixels in the target area Ar in the normal light image WLI, among the pixels in the area Ar' in the fluorescent image IRA and the pixels in the target area Ar in the normal light image WLI.

After step S7, the display control unit 935 sequentially generates video signals for displaying the respective superimposed images (for example, the superimposed image DI illustrated in FIG. 7) sequentially generated by the superimposed image generation unit 934, and sequentially outputs the video signals to the display device 7 (Step S8). As a result, the superimposed images (for example, the superimposed image DI illustrated in FIG. 7) are sequentially displayed on the display device 7.

The first embodiment described above provides the following effect.

The control device 9 according to the first embodiment specifies the target area Ar with the pixel level being equal to or higher than a predetermined threshold (the upper limit value in the first embodiment) in the normal light image WLI. Furthermore, when generating the superimposed image DI by superimposing the corresponding pixels in the normal light image WLI and the fluorescent image IRA on each other, for the area Ar" at the same position as the target area Ar, the control device 9 generates the superimposed image DI only including the pixels in the target area Ar in the normal light image WLI. In other words, the control device 9 generates the superimposed image DI only including the pixels in the target area Ar in the normal light image WLI, for the area Ar" corresponding to the highly reflective portion of the observation target.

Thus, the superimposed image DI may be generated that has no risk of making the viewer recognize the highly reflective portion of the observation target as the lesioned part, and thus is suitable for the observation.

Second Embodiment

Next, a second embodiment will be described.

In the following description, the same reference numerals are given to components that are the same as those in the first embodiment described above, and detailed description thereof will be omitted or simplified.

Figure 8:
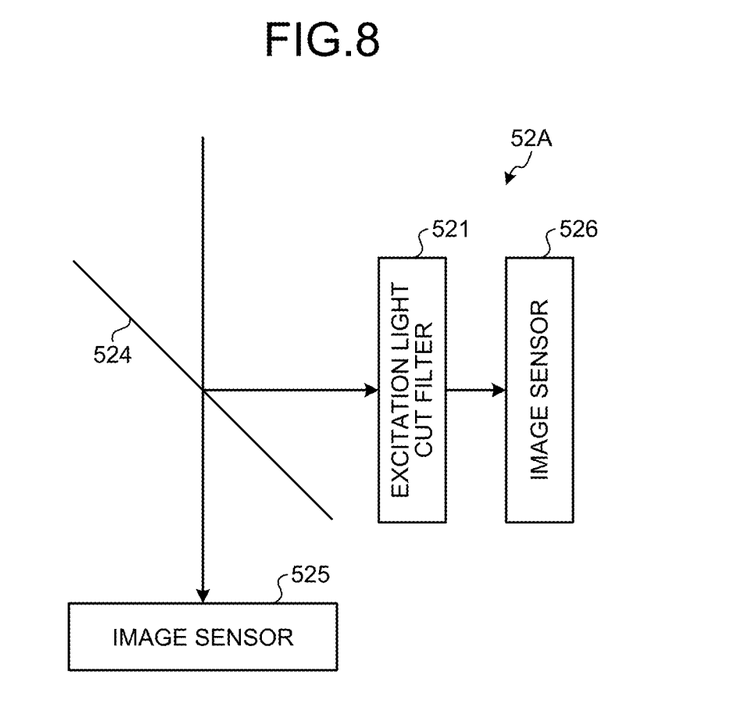
FIG. 8 is a diagram illustrating a configuration of an imaging unit according to a second embodiment.

FIG. 8 is a diagram illustrating a configuration of an imaging unit 52A according to the second embodiment.

In the first embodiment described above, the imaging unit 52 has only one image sensor 522. The control unit 94 drives the first and the second light sources 31 and 32 in a time division manner (so that the light sources emit light in different time periods) and causes the image capturing with the image sensor 522 to be performed in synchronization with the light emission timings of the first and the second light sources 31 and 32. Thus, the normal light image and the fluorescent image are generated.

On the other hand, in the second embodiment, as illustrated in FIG. 8, an imaging unit 52A having two image sensors, that is, first and second image sensors 525 and 526 is used instead of the imaging unit 52. The control unit 94 drives the first and the second light sources 31 and 32 simultaneously (so that the light sources emit light in the same time period) and causes the image capturing with the first and the second image sensors 525 and 526 to be performed in the light emission period of the first and the second light sources 31 and 32. Thus, the normal light image and the fluorescent image are generated.

Specifically, the imaging unit 52A includes a dichroic mirror 524, an excitation light cut filter 521, the first and the second image sensors 525 and 526, and a signal processing unit 523, as illustrated in FIG. 8. In FIG. 8, the signal processing unit 523 is not illustrated for the sake of description.

The dichroic mirror 524 is disposed on the downstream side of the lens unit 51 on the optical path, enables light in the shorter side transmission band of the excitation light cut filter 521 to pass therethrough, and reflects the light in the cut band and the longer side transmission band of the excitation light cut filter 521. Thus, among the first subject image (normal light (white light)) and the second subject image (near-infrared excitation light and fluorescence) obtained through the lens unit 51, the first subject image passes through the dichroic mirror 524 and the second subject image is reflected by the dichroic mirror 524.

The first image sensor 525 is provided on the optical path of the first subject image that has passed through the dichroic mirror 524, and captures the first subject image to generate the normal light image.

The second image sensor 526 is provided on the optical path of the second subject image reflected by the dichroic mirror 524, and captures the second subject image to generate the fluorescent image.

The excitation light cut filter 521 is provided between the dichroic mirror 524 and the second image sensor 526 (the optical path of the second subject image).

The first and the second image sensors 525 and 526 may have the same configuration as the image sensor 522 described in the first embodiment. The second image sensor 526 may be an infrared image sensor only sensitive to the near-infrared wavelength band.

The effects that are the same as those obtained in the first embodiment described above may be obtained also by using the imaging unit 52A according to the second embodiment described above.

Other Embodiments

The embodiments for carrying out the present disclosure have been described above, but the present disclosure should not be limited only by the above-described first and second embodiments.

In the first and the second embodiments described above, the first light source 31 emits white light and the second light source 32 emits near-infrared excitation light. However, the present disclosure is not limited to this. The first and the second light sources 31 and 32 may be configured in any other way, as long as the first light source 31 emits light in a first wavelength band, and the second light source 32 emits light in a second wavelength band different from the first wavelength band. The first and the second wavelength bands may partially overlap or may not overlap at all. Furthermore, the first light source 31 may emit narrowband light.

Photodynamic diagnosis (PDD) is known as one of the cancer diagnostic methods for detecting cancer cells.

For example, the photodynamic diagnosis uses a photosensitive substance such as 5-aminolevulinic acid (hereinafter referred to as 5-ALA). The 5-ALA is a natural amino acid originally contained in living bodies of animals and plants. This 5-ALA is taken up into cells after administration into the body and biosynthesized into protoporphyrin in mitochondria. In cancer cells, the protoporphyrin accumulates excessively. The protoporphyrin that is excessively accumulated in cancer cells is photoactive. Thus, when the protoporphyrin is excited by excitation light (for example, blue visible light in a wavelength band of 375 nm to 445 nm), the protoporphyrin emits fluorescence (for example, red fluorescence in a wavelength band of 600 nm to 740 nm). Such a cancer diagnostic method causing cancer cells to emit fluorescence by using photosensitive substances is referred to as photodynamic diagnosis.

In the first and the second embodiments described above, the first light source 31 may include an LED that emits white light, and the second light source 32 may include a semiconductor laser that emits excitation light (for example, blue visible light in a wavelength band from 375 nm to 445 nm) for exciting protoporphyrin. The same effects as obtained by the first and the second embodiments described above may be obtained also with such a configuration.

In the first and the second embodiments described above, the first and the second periods are set to be repeated alternately. However, the present disclosure is not limited to this. At least one of the first and the second periods may be continuous, and a frequency ratio between the first and the second periods may be set to be different from 1:1.

In the first and the second embodiments described above, the medical image processing device according to the present disclosure is installed in the medical observation system 1 including the insertion portion 2 as a rigid endoscope. However, this should not be construed in a limiting sense. For example, the medical image processing device according to the present disclosure may be installed in a medical observation system including the insertion portion 2 that is a flexible endoscope. Furthermore, the medical image processing device according to the present disclosure may be installed in a medical observation system such as a surgical endoscope (see, for example, Japanese Laid-open Patent Publication No. 2016-42981) for observing a certain field of view area inside a subject (inside a living body) or a surface of the subject (living body surface) with the area enlarged.

In the first and the second embodiments described above, a part of the configuration of the camera head 5 and a part of the configuration of the control device 9 may be provided in, for example, the connector CN1 or the connector CN2.

In the first and the second embodiments described above, the second image processing unit 933 executes the area deleting processing on the fluorescent image IRB, but the present disclosure is not limited to this, and a configuration in which the area deleting processing is not executed may be employed. In such a case, the superimposed image generation unit 934 does not superimpose the area Ar' on the target area Ar when superimposing the corresponding pixels in the normal light image WLI and the fluorescent image IRB on each other. With such a configuration, for the area Ar" at the same position as the target area Ar, the superimposed image generation unit 934 generates the superimposed image DI only including the pixels in the target area Ar in the normal light image WLI, as in the first embodiment described above.

In the second embodiment described above, an IR cut filter may be employed instead of the excitation light cut filter 521. In such a case, the dichroic mirror 524 is configured to enable light in the shorter side transmission band and the cut band of the excitation light cut filter 521 to pass therethrough, and reflects the light in the longer side transmission band of the excitation light cut filter 521. The IR cut filter is provided between the dichroic mirror 524 and the first image sensor 525.

The medical image processing device and the medical observation system according to the present disclosure may generate a superimposed image suitable for observation.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A medical image processing device comprising
a processor comprising hardware, the processor being configured to:
acquire a first image captured based on light from an observation target irradiated with light in a first wavelength band, the observation target emitting fluorescence upon being irradiated with excitation light in a second wavelength band different from the first wavelength band;
acquire a second image captured based on the excitation light and the fluorescence from the observation target irradiated with the excitation light;
perform area identification only on the first image to specify a target area in which a pixel level is equal to or higher than a predetermined threshold, in the first image;
generate a superimposed image by superimposing corresponding pixels in the first image and the second image on each other; and
generate, for an area at a same position as the target area, the superimposed image only including pixels in the target area in the first image, among pixels in the area at the same position as the target area in the second image and pixels in the target area in the first image.

2. The medical image processing device according to claim 1, wherein the processor is configured to specify the target area with the pixel level at an upper limit value, in the first image.

3. A medical observation system comprising:
the medical image processing device according to claim 2 configured to process the first image and the second image; and
an imaging device comprising:
an image sensor configured to
generate the first image captured based on light from the observation target irradiated with light in the first wavelength band, the observation target emitting fluorescence upon being irradiated with excitation light in the second wavelength band different from the first wavelength band, and
generate a second image captured based on the excitation light and the fluorescence from the observation target irradiated with the excitation light; and
a cut filter disposed on an optical path of the excitation light traveling through the observation target to reach the image sensor from the observation target, the cut filter cutting light in a wavelength band that is at least a part of the second wavelength band.

4. A medical observation system comprising:
the medical image processing device according to claim 2 configured to process the first image and the second image; and
an imaging device comprising:
a first image sensor configured to generate the first image captured based on light from the observation target adiated with light in the first wavelength band,
a second image sensor configured to generate the second image captured based on the excitation light and the fluorescence from the observation target irradiated with the excitation light; and
a cut filter disposed on an optical path of the excitation light traveling through the observation target to reach the second image sensor from the observation target, the cut filter cutting light in a wavelength band that is at least a part of the second wavelength band.

5. The medical observation system according to claim 4, further cornpri sing:
a beam splitter arranged in the optical path and splitting light from an observation target into a first separation light incident on the first image sensor and a second separation light incident on the second image sensor.

6. The medical observation system according to claim 5, wherein the beam splitter is a dichroic mirror,
the first separation light is transmitted by the dichroic minor and directed toward the first image sensor, and
the second separated light is reflected by the dichroic mirror and directed to the second image sensor.

7. A medical observation system comprising:
the medical image processing device according to claim 1 configured to process the first image and the second image; and
an imaging device comprising:
an image sensor configured to
generate the first image captured based on light from the observation target irradiated with light in the first wavelength band, the observation target emitting fluorescence upon being irradiated with excitation light in the second wavelength band different from the first wavelength band, and
generate the second image captured based on the excitation light and the fluorescence from the observation target irradiated with the excitations light; and
a cut filter disposed on an optical path of the excitation light traveling through the observation target to reach the image sensor from the observation target, the cut filter cutting light in a wavelength band that is at least a part of the second wavelength band.

8. A medical observation system comprising:
the medical image processing device according to claim 1 configured to process the first image and the second image; and
an imaging device comprising:
a first image sensor configured to generate the first image captured based on light from the observation target irradiated with light in the first wavelength band,
a second image sensor configured to generate the second image captured based on the excitation light and the fluorescence from the observation target irradiated with the excitation light; and
a cut filter disposed on an optical path of the excitation light traveling through the observation target to reach the second image sensor from the observation target, the cut filter cutting light in a wavelength hand that is at least a part of the second wavelength band; and
the medical image processing device according to claim 1 configured to process the first image and the second image.

9. The medical observation system according to claim 8, further comprising:
a beam splitter arranged in the optical path and splitting light from an observation target into a first separation light in the first wavelength band incident on the first image sensor and a second separation light in the second wavelength band incident on the second image sensor.

10. The medical observation system according to claim 9, wherein the beam splitter is a dichroic mirror, the first separation light is transmitted by the dichroic minor and directed toward the first image sensor, and
the second separated light is reflected by the dichroic mirror and directed to the second image sensor.

11. The medical image processing device according to claim 1, wherein the processor is configured to set a luminance value of pixels in the target area in the second image to zero before generating the superimposed image.

* * * * *